United States Patent [19]

Yaeger

[11] Patent Number: 4,685,928

[45] Date of Patent: Aug. 11, 1987

[54] ARTIFICIAL ARM AND HAND ASSEMBLY

[76] Inventor: Ivan Yaeger, 1277 NW. 88 St., Miami, Fla. 33147

[21] Appl. No.: 784,082

[22] Filed: Oct. 4, 1985

[51] Int. Cl.$^4$ ............................................. A61F 2/54
[52] U.S. Cl. ...................................... 623/64; 623/60; 623/25
[58] Field of Search ........................ 623/24.25, 57–65; 901/14, 15; 414/1–9

[56] References Cited

U.S. PATENT DOCUMENTS

| | | | |
|---|---|---|---|
| 3,466,944 | 9/1969 | Motis | 623/24 |
| 3,491,378 | 1/1970 | Ioffe | 623/60 |
| 4,016,607 | 4/1977 | Pihlaja | 623/57 |
| 4,149,278 | 4/1979 | Wiher et al. | 414/4 |
| 4,291,421 | 9/1981 | Massey | 623/57 |
| 4,367,532 | 1/1983 | Crum | 901/15 |

Primary Examiner—Richard J. Apley
Assistant Examiner—James Prizant
Attorney, Agent, or Firm—John Cyril Malloy

[57] ABSTRACT

An artificial arm capable of being used as a prosthesis on a human body and controlled through activating sensors secured to the human body adjacent the attachment site of the artificial arm and operating a plurality of drive motors. Three independent drive motors are mounted between foundation bases including an upper arm base, forearm base and hand base wherein the latter two move relative to one another and to the forearm base and each of the three drive motors are positioned and structured to cause relative movement of one foundation base relative to the other, thereby adding strength and simplicity to an artificial arm structure having a high degree of versatility and range of movements.

10 Claims, 7 Drawing Figures

ARTIFICIAL ARM AND HAND ASSEMBLY

BACKGROUND OF THE INVENTION

1. Field of the Invention

An artificial arm assembly of the type incorporating a plurality of individual drive motors to accommodate a preselected movement of a forearm base relative to an upper arm base, a hand base relative to the forearm base and digits, representing fingers, relative to the hand base.

2. Description of the Prior Art

Artificial members of the human body have reached a relatively sophisticated stage of development in the prior art. As a result, members include artificial arms and artificial hands serving as prosthesis and specifically designed to be operatively attached to the human body in replacement for the missing limb. Specifically with regard to the design and operation of such artifical hands and arm assemblies, including mechanically movable fingers, such are designed to attempt freedom of movement resembling as closely as possible the movement of the natural arm and hand. More specifically, the mechanically movable fingers are intended to enable the user thereof to perform the many gripping functions normally occurring in day-to-day use. One factor is of course operational time required to perform each function. Obviously, such operational time should be minimized in an attempt to normalize the movement and time of such movement relative to the natural limb.

In order to minimize the operational time of artificial limbs and increase and vary the range of movement of such artificial limbs, especially the gripping fingers, it is necessary to provide a drive assembly for the movable element which is efficient.

Representative attempts existing in the prior art to meet the foregoing requirements are varied. Included are pneumatic drive systems which receive the driving energy from high pressure containers or air pressure conduits. Even gas pressure cartridges have been used as the energy supply for artificial limbs. German Patent Publication (DOS) No. 2433710 illustrates a device employing high pressure containers which are rechargeable.

Other known drive assemblies are disclosed in an additional German Patent Publication (DOS) No. 2426711 demonstrating the use of an electric motor connected to the drive means for operating fingers of an artificial hand by means of cord and pulley assemblies. Also, the U.S. Pat. No. 4,188,166 to Moreau demonstrates a small size telemanipulator with a rotatable gripping tool secured to the end thereof. The latter structure is primarily used for a gripping tool rather than as a prosthesis for the replacement of a missing limb. However, the structures are similar in the sense that arm and hand movement and gripping force are intended to duplicate that of a human arm and hand.

Other U.S. patents which demonstrate arm and limb assemblies including a variety of drive means used to accomplish the aforementioned requirements include Motis, U.S. Pat. No. 2,516,791; Fishbein, U.S. Pat. No. 2,537,338; Alderson, U.S. Pat. No. 2,592,842; Motis, U.S. Pat. No. 3,466,944; Yakobson et al, U.S. Pat. No. 3,521,303; Eroyan, U.S. Pat. No. 4,094,016; Moreau, U.S. Pat. No. 4,188,166; Janovsky, U.S. Pat. No. 4,232,405; and Pinson, U.S. Pat. No. 4,246,661.

The structures disclosed in the above noted domestic and foreign patents represent a segment of the prior art of artificial hand and limb assemblies which are specifically designed to improve the range and variety of motions as well as speed of operation and gripping pressure in order to allow a prosthesis structure to more closely resemble the workings of a natural hand and arm.

SUMMARY OF THE INVENTION

The present invention is directed towards an artificial arm and hand assembly designed to be mounted on the human body in replacement of the missing limb. The subject assembly comprises foundation means comprising an upper arm foundation base, a forearm foundation base and a hand base. Each of these foundation bases are movably connected to the next adjacent foundation base in a normal sequential disposition. More specifically, the upper arm base is pivotally connected to the forearm base at a junction therebetween disposed generally at the elbow. Similarly, the forearm base is movably connected to the hand base generally at the wrist section of the assembly.

An important feature of the present invention is the design and structure of the drive means which allows relative movement of the forearm relative to the upper arm and the hand relative to the forearm and accordingly the upper arm as well. Such drive means includes three spaced apart independently operated and controlled drive motors and accompanying gear assembly. More specifically, a first drive motor drivingly engages the first gear assembly. The drive motor and accompanying structure is fixedly mounted on the upper arm and the first gear assembly is disposed in interconnecting relation with the power output of the first drive motor and the correspondingly positioned end of the forearm foundation base. Accordingly, activation of the first motor cause movement of the forearm base relative to the upper arm base. The second drive motor, defining part of the drive means, is mounted on the forearm foundation base so as to travel therewith. A second gear assembly is interconnected in driven relation to the power output of the drive motor and further is interconnected to rotate an elongated shaft means having its distal end fixedly secured to the hand base. Therefore, activation of the second drive motor and the accompanying second gear assembly causes rotation of the hand base relative to the forearm base about the longitudinal axis of the latter. Finally, a third drive motor is mounted on the hand base so as to move therewith. A third gear assembly accompanies the third drive motor and is driven thereby and defines driven interconnection between the output of the third drive motor and a plurality of the digits. A single digit, preferably in the form of a thumb, is fixedly secured to the hand base and pivotal movement between the movable digits and the fixed digits provides a gripping action. The force of the gripping action is regulated by the activation of the third drive motor.

Control means for the drive motors may take a plurality of configurations. More specifically, during actual use and attachment to the body, a plurality of nerve and/or muscle sensors are secured operatively in attachment to appropriate locations to the skin of the wearer of the subject assembly. The opposite ends are secured directly to the drive motor for activation thereof. Sensors of the type mentioned herein are available commercially by the Viennatone Corporation and operate in two phases. One sensor or sensor pair is based on activation by muscle contraction and an electrical pulse is generated thereby. This in turn is translated to a power amplifier or directly to the motor, dependent upon electrical control circuitry provided, so as to activate the independent drive motors. Similarly, a second pair of sensors are activated by nerve impulses generating certain electrical pulses which are then transferred by appropriately connected conductors to a power amplifier and then to the respective drive motors involved. By virtue of this type of facility, the arm and the hand assembly can be operated "automatically" based on muscle contraction and/or nerve impulses picked up by the body mounted sensors. Therefore, the forearm foundation can be moved relative to the upper arm foundation independently or concurrently with movement of the hand foundation to resemble or duplicate the movement of the natural missing limb.

Alternately, demonstration of the assembly may be accomplished by a control console or unit powered by a conventional electrical source outlet and interconnected independently to the three drive motors such that the hand and arm assembly may be demonstrated through its complete range of movement without being mounted on an actual patient or user.

BRIEF DESCRIPTION OF THE DRAWINGS

For a fuller understanding of the nature of the present invention reference is had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
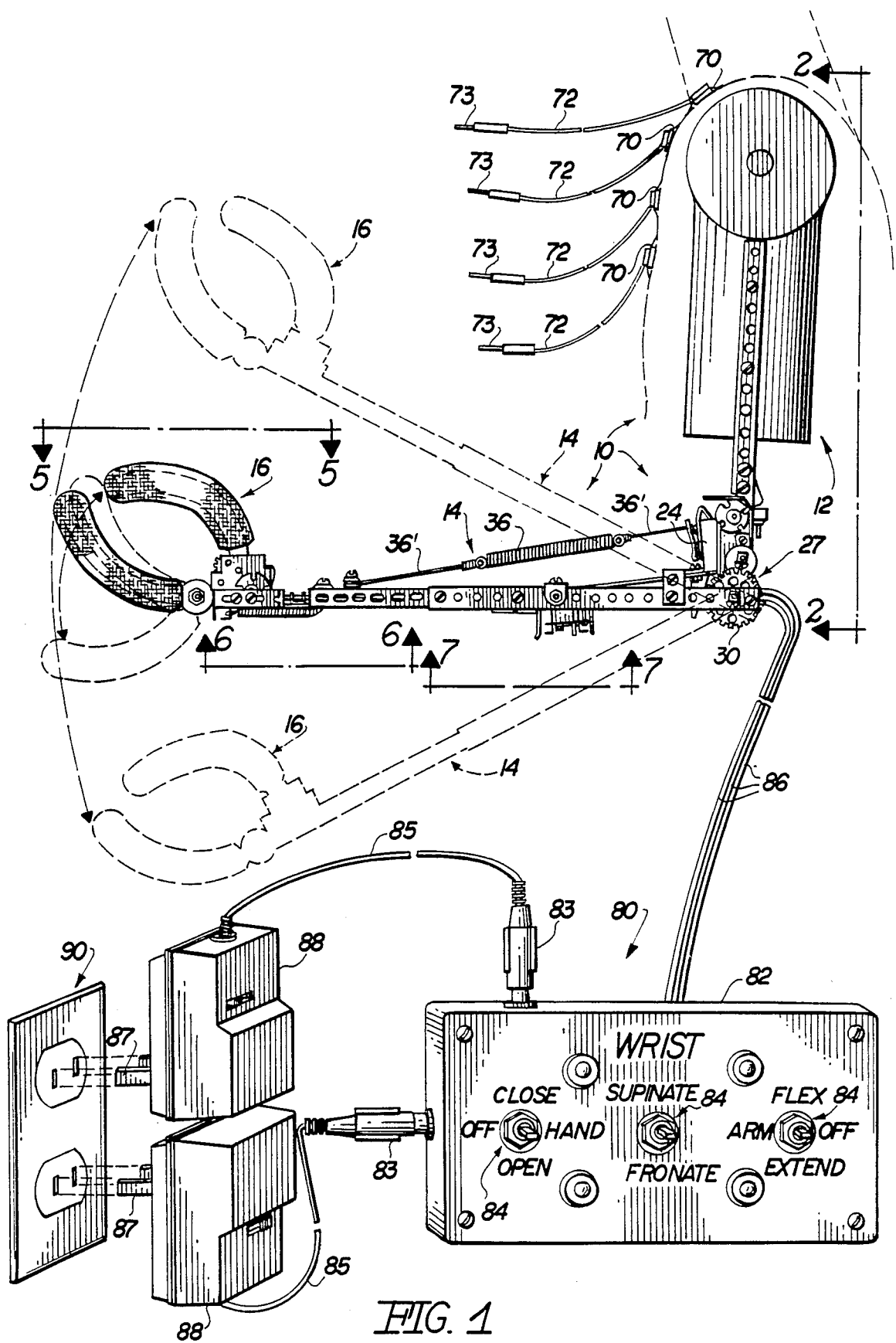
FIG. 1 is a side view of the artificial arm and hand assembly of the present invention shown in its range of movements represented in phantom lines and mounted on a patient also represented in phantom lines with various embodiments of the control assembly associated therewith.
Figure 3:
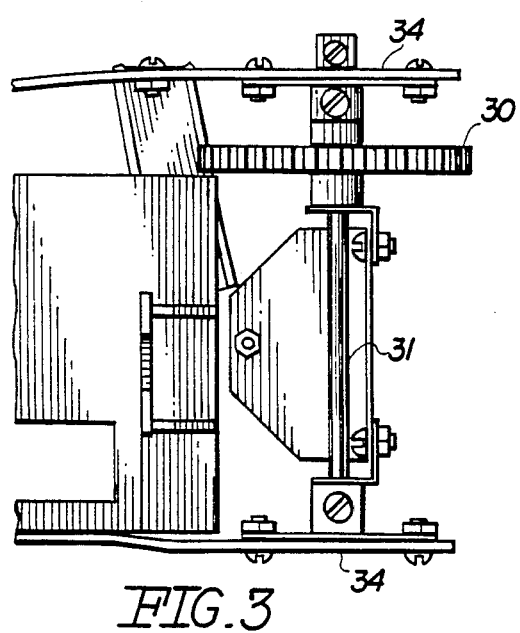
FIG. 3 is a bottom plan view in partial cutaway of an interconnection between the forearm and the upper arm foundation of the present invention.
Figure 2:
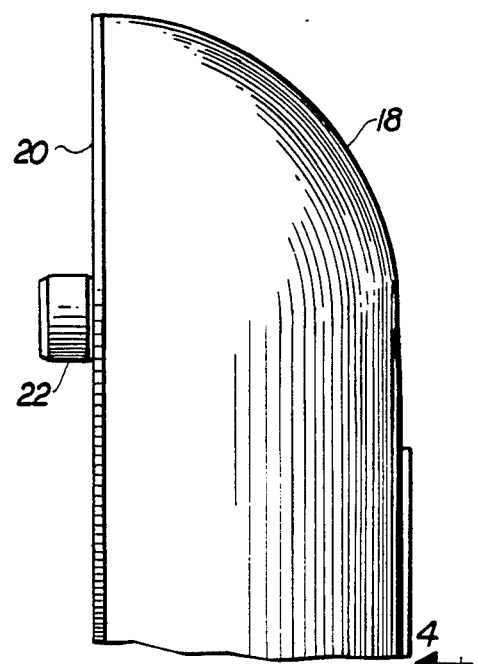
FIG. 2 is a rear plan view along line 2—2 of FIG. 1 of the upper arm base portion of the present invention.
Figure 4:
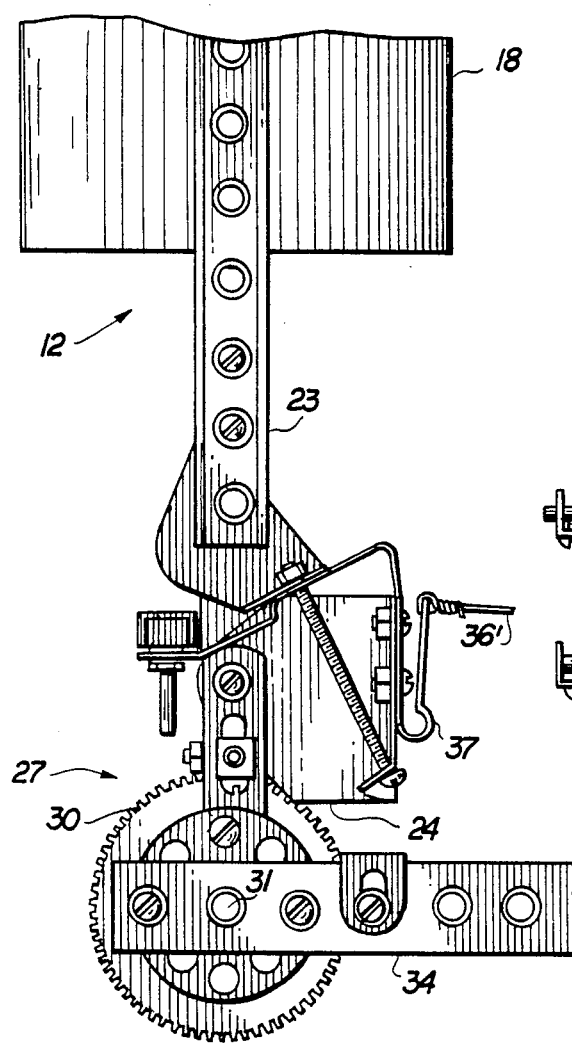
FIG. 4 is a side plan view in partial cutaway along line 4—4 of FIG. 2 showing interconnection of the forearm base foundation and the upper arm base foundation at a location generally in the area of the elbow of the artificial arm and hand assembly of the present invention.

As shown in FIGS. 1 through 7, the artificial arm and hand assembly of the present invention is generally indicated as 10 and includes foundation means in the form of a plurality of foundation bases. More specifically, the foundation includes an upper arm base 12, a forearm base, generally indicated as 14, and a hand base, generally indicated as 16. With reference to FIGS. 2, 3, and 4, the upper arm foundation base 12 includes a free end portion 18 which may be generally shaped to conform to the configuration of a shoulder and which includes a mounting face 20 with a protruding connector element 22. The actual configuration and structure of the face 20 and connector element 22 may vary dependent upon the portion of the shoulder and/or arm stub to which the upper arm base 12 is attached. The upper arm base 12 includes a support platform 23 extending downwardly from the free end 18 and terminating in a junction end 25 located at an elbow type junction 27 associated with the arm portion of the assembly and generally indicated in FIG. 4. The support platform 23 is supportingly connected to a first drive motor 24 which forms a part of the drive means to be described in detail hereinafter. The drive motor 24 is secured to have a power take-off (not clearly shown) disposed in driving engagement with a gear assembly generally indicated as 26 interconnected to one another to accomplish proper and desired mechanical advantage and speed reduction for the rotation of a drive shaft 29. The drive shaft 29 drivingly engages a primary drive gear 30 secured to a connecting shaft or axle 31. The primary drive gear 30 is fixedly secured so as to rotate with or cause rotation of the axle 31 which in turn is connected to a correspondingly positioned end 34 of the forearm foundation base 34. By virtue of this interconnection and the cooperative engagement between the first drive motor 24 and the first gear assembly generally indicated as 26 as well as the primary drive gear 30, relative movement of the forearm base relative to the upper arm base is permitted upon activation of the first drive motor 24.

The assembly comprises biasing means partially defined by a first biasing element 36 preferably in the form of a spring element having its opposite ends secured by attachment facilities 36' to the upper arm base 12 and the forearm base 14 respectively. By virtue of the placement of the first biasing element 36, the forearm base as well as the hand base is normally biased into a position generally into a bent position relative to the elbow location 27 or junction between the upper arm base 12 and the forearm base 14. With reference to FIG. 4, the correspondingly positioned connecting facility or structure 36' is mounted to a spring-like attachment member 37 secured to the upper arm base 12 as shown.

With reference to FIGS. 1, 5, 6 and 7, the forearm base 14 has one end 34 movably connected to the upper arm base 12 as set forth above. The opposite end 39 is movably attached to the hand base 16 as will be explained in greater detail hereinafter. The forearm base 14 comprises a support platform or structure extending along its length and indicated generally as 40. The support structure of the forearm base has a longitudinal dimension generally equivalent to the length of the forearm dependent on the size of the patient or person on which the subject artificial arm and hand assembly are mounted. Further, the support structure 40 serves to supportingly engage a second drive motor 42 cooperatively interconnected to a second gear assembly generally indicated as 41 comprising a plurality of reduction and lever gears which ultimately cause the rotation of elongated drive shaft 44 extending substantially along the length of the support structure 40. The drive shaft 44 is rotatably driven by coupling 45 which in turn is fixed to rotate with drive axle 47. Drive axle 47 is of course driven by activation and forced rotation of the gear assembly 41 based on power take-off 46 of second drive motor 42 driving a primary drive gear 43. Activation of the second drive motor 42 causes rotation of the elongated drive shaft 44 in either direction, based upon the direction of rotation of the drive motor 42. The distal end 44' (see FIG. 5) is fixedly secured to the hand base 16 so as to cause rotation thereof in either preselected opposite directions based upon the direction of rotation of the second drive motor 42. Accordingly, the hand base 16 rotatates relative to the distal end 39 of the support structure 40 of the forearm base 14. This rotational movement is generally similar to the range of movement of the hand relative to the forearm about a natural wrist in the human hand-forearm connection. Further, this rotational movement is somewhat limited by an additional biasing element 49 having its opposite ends 50 and 51 attached to the hand base 16 and the distal end 39 of the forearm base 14 respectively. By virtue of this connection and the specific position of the biasing element or spring 49, the rotation of the hand in a counterclockwise direction relative to the longitudinal axis of the forearm or the length and diposition of the drive shaft 44 is limited similar to the limited range of rotation of the natural hand about the wrist and distal end of the forearm.

Figure 5:
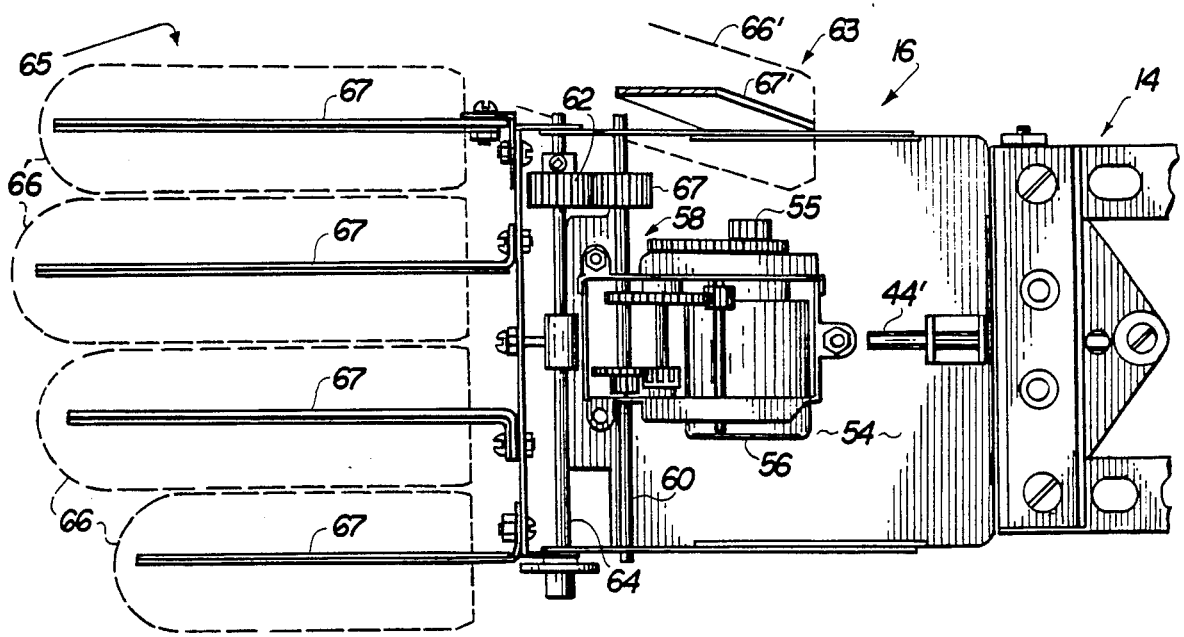
FIG. 5 is a top plan view in partial cutaway along line 5—5 of FIG. 1 of the hand base foundation of the present invention with digits represented in phantom lines.
Figure 6:
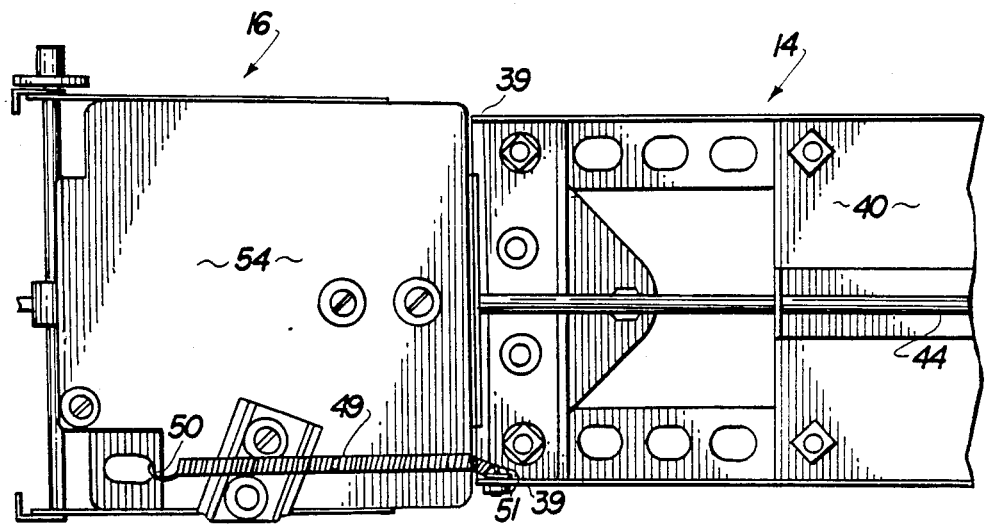
FIG. 6 is a bottom plan view in partial cutaway along line 6—6 of FIG. 1 without the digits being represented.
Figure 7:
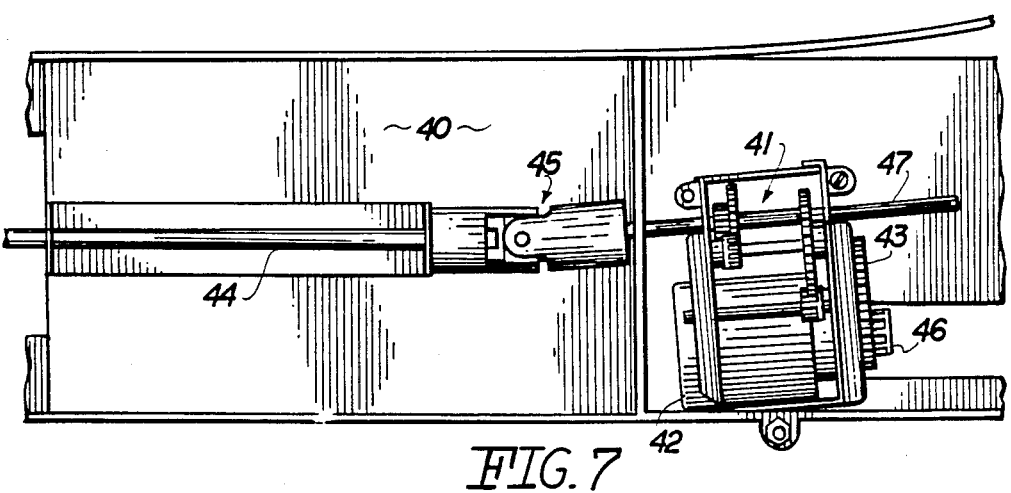
FIG. 7 is a bottom plan view in partial cutaway along line 7—7 of FIG. 1 showing a detailed structure of the forearm base foundation of the present invention.

Again with primary reference to FIGS. 5 and 6, the hand base 16 includes a support platform or structure 54 which is fixedly secured to the distal end 44' of the drive shaft 44 such that the support structure 54 rotates therewith in the manner described above. A third drive motor 56 including power take-off 57 is drivingly interconnected to a third gear assembly 58 driven by rotation of power take-off 55 and rotation of third drive motor 56. Upon activation and rotation of the third gear assemby 58, drive sha4ft 60 is rotated in the appropriate direction. Intermeshing drive gears 61 and 62 serve to cause rotation of support shaft 64 upon rotation of drive shaft 60. The rotation of support shaft 64 causes rotation or pivotal movement in the appropriate direction of a digit assembly generally indicated as 65. Digit assembly 65 includes an appropriate number, preferably four, of digit frames 67. Each of the digit frames 67 is covered by a soft, pliable covering representing a finger and being specifically structured to enable gripping or grasping of a variety of objects. A fifth digit, preferably in the form of a thumb is generally indicated as 63 and includes a thumb frame 67' surrounded by a similar, pliable flexible material 66' similar to that covering the digit frames 67. The thumb frame 67' is fixedly secured to the support structure 54 of hand base 16. Further, the thumb frame 67' and covering 66' are structured to be angled outwardly generally towards the digit assembly 65. Accordingly, upon rotation of the support shaft 64 in the appropriate direction, the digit assembly 65 will be rotated or pivoted towards and away from the thumb respectively thereby defining a gripping and releasing position of the hand base 16 respectively.

It should be emphasized that each of the first, second and third drive motors, 24, 42 and 56 respectively are capable of being driven in reverse directions of rotation such that the respective components which the first, second and third drive motors position may be disposed in either of two directions based upon the direction of rotation of the respective drive motor.

Again with primary reference to FIG. 1, the control means of the present invention includes two embodiments respectively capable of operating the artificial arm and hand assembly 10 of the present invention while fitted to a patient or while being demonstrated prior to being fitted to a patient or user. More specifically, the control means of the present invention includes a plurality of contact sensors 70 secured directly to the body as generally shown and represented in FIG. 1. These sensors are interconnected to electrical conductors 72 and are attached by appropriate connectors 73 to predetermined ones of the first, second and third drive motors. By virtue of this connection and by virtue of the specific structure of the sensor 70, muscle contraction and/or nerve impulses generated by the intention to move the artificial arm in the user's body creates an electrical pulse. This pulse is transferred through conductors 72 and connector 73 to the appropriate drive motors. The drive motors are then activated in either of two opposite or reverse directions in order to manipulate the appropriate foundation base 12, 14, and 16 to position the arm as desired. The sensors 70 again may take the form of the type which react to muscle contractions or alternately, the type which react to nerve impulses. Both of these types of sensors are commercially available and manufactured by the Viennatone Corporation.

Yet another embodiment of the present invention is generally indicated as 80 and includes a control console 82 having one or more operative switches 85 each designed to operate separate ones of the first, second and third drive motors. Interconnection to the respective drive motors occurs by the plurality of conductors 86. The console 82 is interconnected to a conventional electrical outlet 90 which is attached to an electrical power supply in the normal fashion. Current regulating devices 88 include plug structures 87 and are interconnected by conductors 85 and plugs 83 to the console 82. Obviously, other power sources could be utilized. Accordingly, with the use of the control assembly 80 demonstration of the artificial arm and hand assembly 10 can be accomplished prior to mounting on a patient as generally pictured in FIG. 1.

It is therefore to be understood that the following claims are intended to cover all of the generic and specific features of the invention herein described, and all statements of the scope of the invention which as a matter of language, might be said to fall therebetween.

Now that the invention has been described,

What is claimed is:

1. An artificial arm and hand assembly of the type capable for use as a prothesis, said assembly comprising:
    (a) a foundation means for supporting of components of the assembly thereon and comprising a plurality of foundation bases including an upper arm base, a forearm base and a hand base,
    (b) each of said bases movably interconnected to a next adjacent base and said plurality of foundation bases collectively disposed into an array resembling a human arm and hand structure,
    (c) drive means mounted on said foundation means and interconnected in driving engagement with preselected ones of said foundation bases for movement thereof,
    (d) said hand base comprising a plurality of digits attached thereto including at least one of said digits fixedly secured to said hand base and a remainder of said plurality of digits movably mounted thereon relative to said one fixedly secured digit,
    (e) wherein said drive means comprises a first drive motor mounted on said upper arm base and movable therewith and drivingly interconnected to said forearm base for pivotable movement thereof relative to said upper arm base, (f) said drive means further comprising a second drive motor mounted on said forearm base and movable therewith and drivingly interconnected to said hand base for rotational movement thereof relative to said forearm base, (g) said drive means further comprising a third drive motor mounted on said hand base and movable therewith and drivingly interconnected to said movably mounted digits for pivotal movement thereof relative to said one fixedly secured digit, (h) activation means electrically connected, independently to each of said drive motors for independent and concurrent activation thereof, (i) retaining means interconnected between at least two of said adjacently positioned foundation bases for limiting movement of one adjacent foundation base relative to the other, (j) said retaining means comprising two biasing elements, the first of which is secured at opposite ends thereof to said upper arm base and said forearm base, said first biasing element disposed and structured to bias said forearm base towards said upper base and limit movement of the former from the latter, and a second biasing element secured at substantially opposite ends thereof to said forearm base and said hand base and including a length thereof disposed in interruptive engagement with a face of said hand base, said second biasing element structured to limit rotational movement of said hand base in opposite directions of rotation relative to said forearm base, and (k) whereby selected ones of said foundation bases and said movably mounted digits are movable independently and concurrently relative to one another.

2. An assembly as in claim 1 wherein each of said first, second and third drive motors are electrically powered and structured for reverse drive, said drive motors electrically connected to said activation means and a power source associated therewith.

3. An assembly as in claim 1 said activation means comprises a switch assembly electrically interconnected to said drive motor, said switch assembly connectable to conventional electric power source via current regulating means for regulating current flow through said switch assembly to said drive motors, whereby said artificial arm may be operated remotely.

4. An assembly as in claim 1 wherein said activating means comprises a plurality of sensor secured to said human body substantially adjacent an area of attachment of said artificial arm to the body, said plurality of sensors including a pair of sensors attached in actuating relation to each of said drive motors, microprocessor means electrically interconnected between each sensor pair and a respective pair of one of said drive motors for regulating current therebetween.

5. An assembly as in claim 4 wherein said plurality of sensors are structured to receive electrical impulses from muscle contraction of the body adjacent said attachment site of said assembly to the body.

6. An assembly as in claim 4 wherein said plurality of sensors are structured to receive electrical impulses from nerves disposed in contracting relation with sensor pairs attached to independent ones of said drive motors.

7. An artificial arm and hand assembly of the type capable for use as a prosthesis, said assembly comprising:

(a) a foundation means for supporting of components of the assembly thereon and comprising a plurality of foundation bases including an upper arm base, a forearm base and a hand base, (b) each of said bases movably interconnected to a next adjacent base and said plurality of foundation bases collectively disposed into an array resemling a human arm and hand structure, (c) drive means mounted on said foundation means and interconnected in driving engagement with preselected ones of said foundation bases for movement thereof, (d) said hand base comprising a plurality of digits attached thereto including at least one of said digits fixedly secured to said hand base and a remainder of said plurality of digits movably mounted thereon relative to said one fixedly secured digit, (e) wherein said drive means comprises a first drive motor mounted on said upper arm base and movable therewith and drivingly interconnected to said forearm base for pivotable movement thereof relative to said upper arm base, (f) said drive means further comprising a second drive motor mounted on said forearm base and movable therewith and drivingly interconnected to said hand base for rotational movement thereof relative to said forearm base, (g) said drive means further comprising a third drive motor mounted on said hand base and movable therewith and drivingly interconnected to said movably mounted digits for pivotal movement thereof relative to said one fixedly secured digit, (h) activation means electrically connected, independently to each of said drive motors for independent and concurrent activation thereof, (i) a first gear assembly disposed at an elbow joint and structured to define a pivotal interconnection between said upper arm base and said forearm base at correspondingly positioned ends thereof, said first gear assembly comprising a drive gear connected in directly driven relation to an output shaft of said first drive motor and drivingly engaging a plurality of regulating gears, said plurality of regulating gears drivingly engaging a driven gear fixedly secured to said correspondingly positioned end of said forearm base and movable therewith, (j) a second gear assembly mounted on said forearm base for movement therewith and connected in driven engagement with said drive motor; a shaft meanns rotatably interconnected between said second gear assembly and said hand base for rotation of the latter relative to said forearm base, (k) said second gear assembly comprising a drive gear connected in directly driven relation to an output shaft of said second drive motor and drivingly engaging a plurality of regulating gears, said plurality of regulating gears drivingly engaging a driven gear fixedly secured to said shaft means, (l) said shaft means comprising an elongated configuration extending from driving interconnection with said second gear assembly at an intermediate location along said forearm base to a distal end of said shaft means drivingly attached to said hand base and secured thereto so as to rotate therewith (m) whereby selected ones of said foundation bases and said movably mounted digits are movable independently and concurrently relative to on another.

8. An assembly as in claim 7 further comprising a third gear assembly mounted on said hand base and movable therewith and in driven engagement with said second drive motor, said third drive gear assembly comprising a drive gear connected in directly driven relation to an output shaft of said third drive motor and drivingly engaging a plurality of regulating gears, said plurality of regulating gears drivingly engaging a support shaft on which said remainder of said plurality of digits are secured.

9. An assembly as in claim 8 wherein said hand base includes said support shaft rotatably mounted thereon, said remainder of movable digits fixedly secured in supported relation on said support shaft and movable therewith, said support shaft fixedly secured to a driven gear comprising one gear of said third gear assembly, said driven gear interconnected in driven relation via the remainder of said third gear assembly, to said third drive motor.

10. An assembly as in claim 9 wherein said remainder of said movable digits are selectively positionable between a gripping position and a released position, said gripping position defined by close proximity of said remainder of movable digits with said one fixedly secured digit, said release position defined by spaced apart disposition of said remainder of movable digits and said one fixedly secured digit.

* * * * *